(12) United States Patent
Ishibiki

(10) Patent No.: US 6,869,394 B2
(45) Date of Patent: Mar. 22, 2005

(54) FITTING JIG OF ENDOSCOPE HOOD MEMBER

(75) Inventor: Kota Ishibiki, Hachioji (JP)

(73) Assignee: Olympus Corporation (JP)

( * ) Notice: Subject to any disclaimer, the term of this patent is extended or adjusted under 35 U.S.C. 154(b) by 42 days.

(21) Appl. No.: 10/255,017

(22) Filed: Sep. 24, 2002

(65) Prior Publication Data

US 2003/0088155 A1 May 8, 2003

(30) Foreign Application Priority Data

Oct. 18, 2001 (JP) ........................................ 2001-321137

(51) Int. Cl.7 ................................................ A61B 1/00
(52) U.S. Cl. .................. 600/127; 600/121; 600/129
(58) Field of Search ................................ 600/121, 127, 600/129, 160, 163, 171, 172, 173, 175, 176

(56) References Cited

U.S. PATENT DOCUMENTS 5,707,344 A * 1/1998 Nakazawa et al. .......... 600/127

FOREIGN PATENT DOCUMENTS

| JP | 57-136430 | 8/1982 |
| JP | 11-206702 | 8/1999 |
| JP | 2000-180735 | 6/2000 |
| JP | 2001-224550 | 8/2001 |

OTHER PUBLICATIONS

Office Action issued by Japanese Patent office on Aug. 19, 2003 in prosecution of corresponding Japanese Patent Application No. 2001-292360.

English translation of Office Action issued by Japanese Patent Office on Aug. 19, 2003 in prosecution of corresponding Japanese Patent Application No. 2001-292360.

* cited by examiner

*Primary Examiner*—Beverly M. Flanagan
(74) *Attorney, Agent, or Firm*—Ostrolenk, Faber, Gerb & Soffen, LLP

(57) ABSTRACT

It is provided a hood member fitting jig to mount a hood member on the end section of an inserted section of an endoscope. The hood member fitting jig includes a base section, a first position regulating section provided on the base section to regulate the position of the hood member with respect to the hood member fitting jig, and a second position regulating section provided on the base section to regulate the position of the hood member fitting jig with respect to an end section of the endoscope.

24 Claims, 12 Drawing Sheets

FITTING JIG OF ENDOSCOPE HOOD MEMBER

CROSS-REFERENCE TO RELATED APPLICATIONS

This application is based upon and claims the benefit of priority from the prior Japanese Patent Application No. 2001-321137, filed Oct. 18, 2001, the entire contents of which are incorporated herein by reference.

BACKGROUND OF THE INVENTION

1. Field of the Invention

The present invention relates to a fitting jig of an endoscope hood member used to fit the hood member at an end portion of an inserted portion of an endoscope.

2. Description of the Related Art

A conventional example of an endoscope apparatus for use in an operation is formed by disposing an objective lens, a light guide, an air and water supply port, and a suction port in an end portion of an inserted portion of an endoscope. Such an endoscope apparatus irradiates a subject such as living tissue with light from the light guide and allows the lighted subject to be viewed via the objective lens so as to suck, through the suction port, air, water, or other material fed through the air and water supply port.

In this regard, when an attempt is made to insert the endoscope into, for example, the stomach, the mucous membrane of the stomach often contacts with and covers the objective lens provided in the end portion of the inserted portion of the endoscope. Thus, more inner areas of the stomach can no longer be viewed.

Correspondingly, Jpn. Pat. Appln. KOKAI Publication No. 11-206702 discloses an end structure of an endoscope in which the end portion of the inserted portion of the endoscope is provided with a guide portion to prevent the mucous membrane from covering the objective lens to block the view. The guide portion of the end structure of the endoscope is a hood-like member having an inner peripheral surface gradually widened so as to draw a curve starting from an end surface of its end portion.

It is assumed that with an endoscope apparatus formed so that a hood member can be freely installed on and removed from an end portion of an endoscope, when the hood member is installed in the end portion of the endoscope, the end portion is insufficiently pressed into the hood member. Then, the hood member projects further from its regular position to cause a larger part of the hood member to come into view. Conversely, if the hood member is installed so that the hood member does not project enough to reach its regular position, the hood member becomes less effective.

Further, with the endoscope apparatus formed so that the hood member can be freely installed on and removed from the end portion of the endoscope, if the hood member is shaped to fit the view, it may be installed at a position different from its regular position in a rotating direction. Consequently, a larger part of the hood member comes into view.

BRIEF SUMMARY OF THE INVENTION

It is an object of the present invention to provide a fitting jig of an endoscope hood member which allows the hood member to be easily and precisely installed on an endoscope.

According to an aspect of the invention, there is provided a fitting jig of an endoscope hood member, the fitting jig comprising a base section, a first position regulating section provided on the base section to regulate a position of the hood member with respect to the hood member fitting jig, and a second position regulating section provided on the base section to regulate a position of the hood member fitting jig with respect to an end section of the endoscope.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the embodiments given below, serve to explain the principles of the invention.

DETAILED DESCRIPTION OF THE INVENTION

Embodiments of the present invention will be described below with reference to the drawings.

(First Embodiment)

Figure 1:
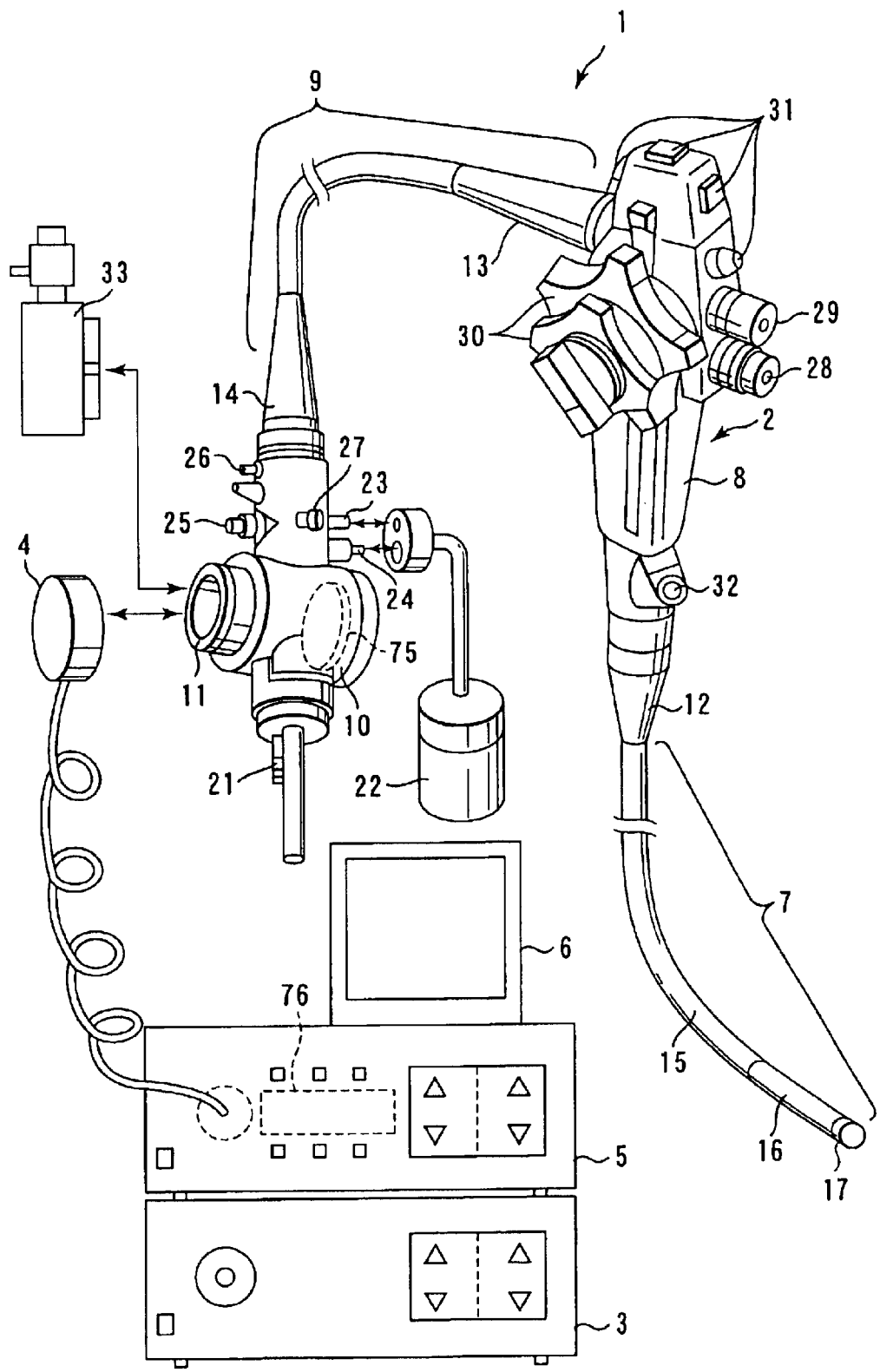
FIG. 1 is a view illustrating the entire configuration of an endoscope apparatus according to a first embodiment of the present invention.
Figure 2:
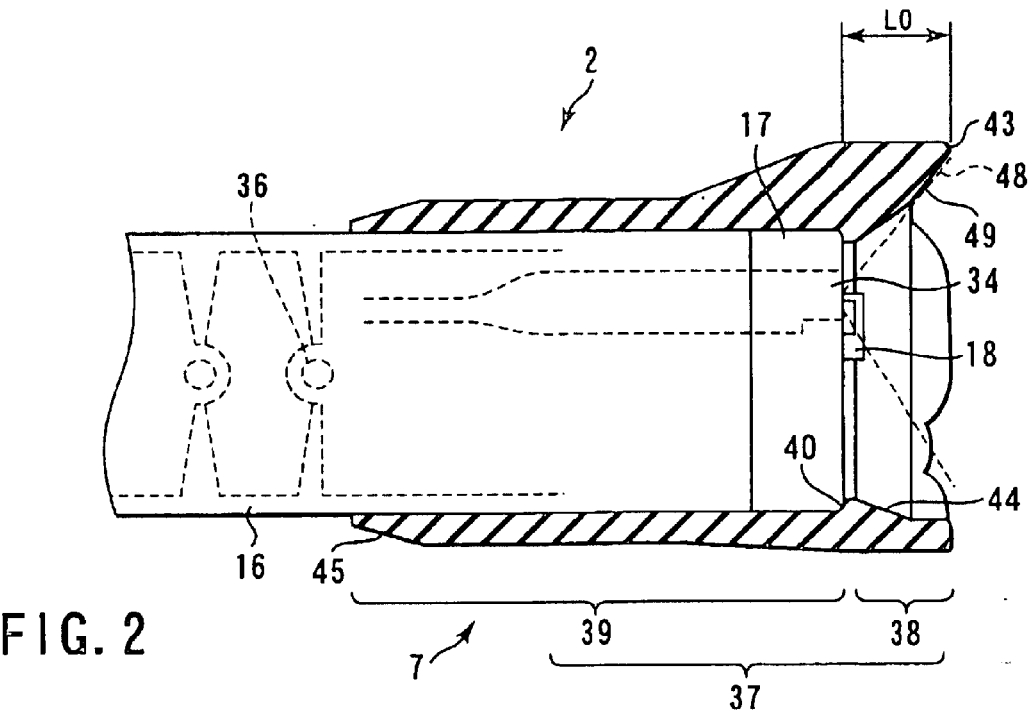
FIG. 2 is a sectional view of an end portion of the first embodiment in FIG. 1.
Figure 3:
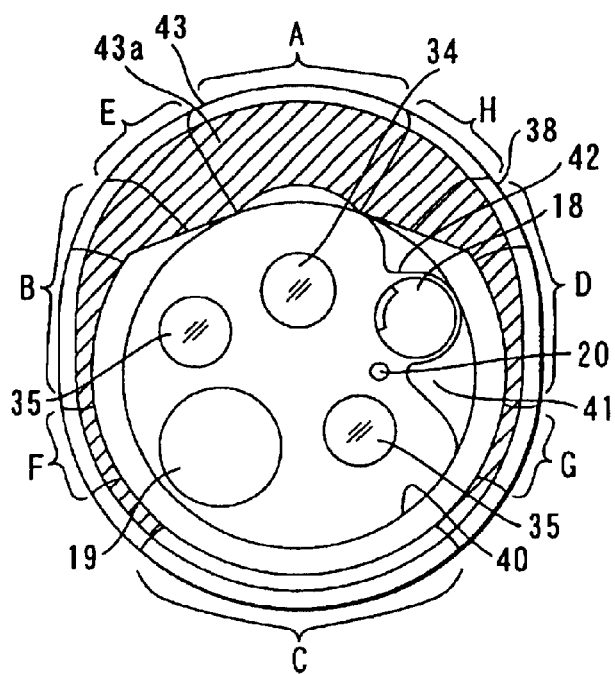
FIG. 3 is a front view of the end portion of the endoscope of the first embodiment in FIG. 1.
Figure 4:
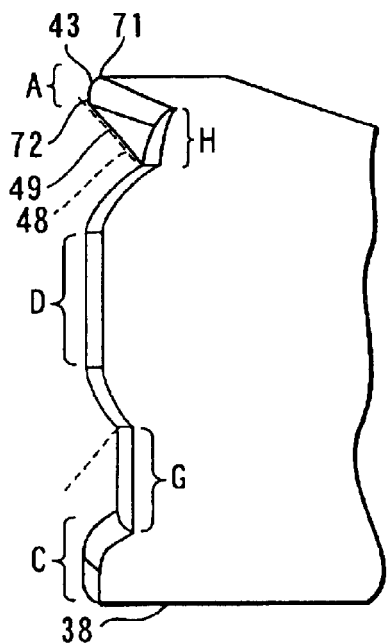
FIG. 4 is a side view showing a hood member removably connected to the end portion of the endoscope of the first embodiment in FIG. 1.
Figure 5:
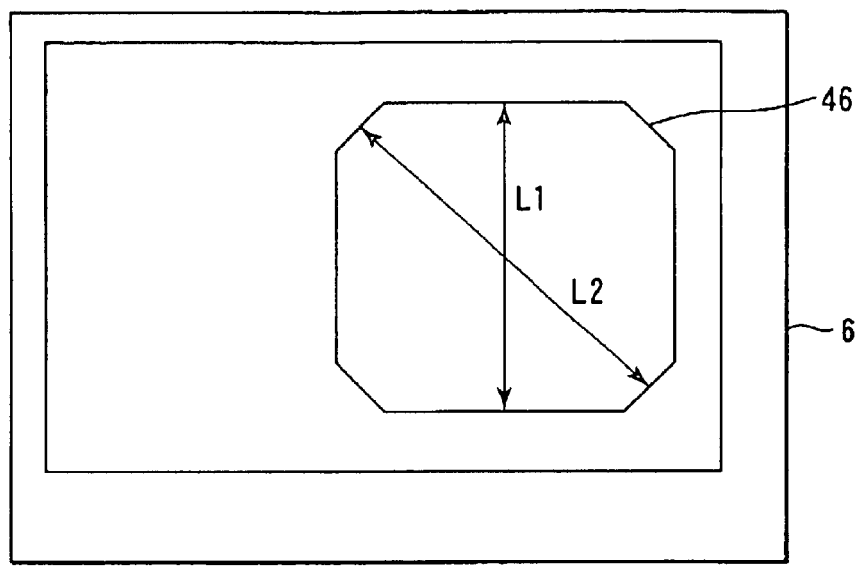
FIG. 5 is a plan view showing an observed image displayed on a monitor according to the first embodiment of the present invention.
Figure 6:
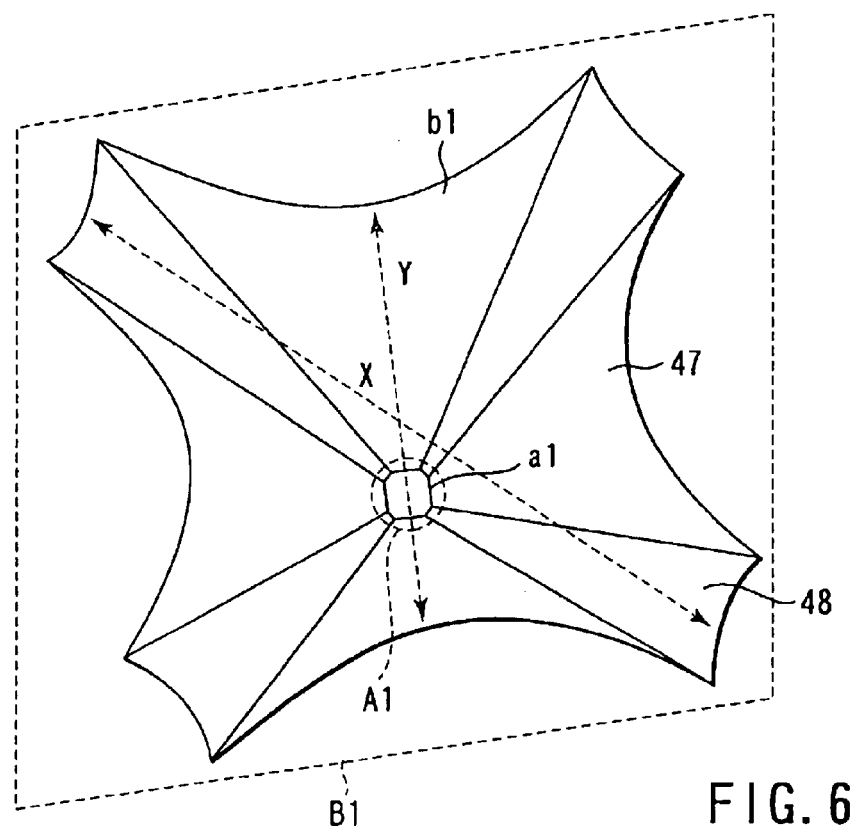
FIG. 6 is a view illustrating an observation view area used if the observed image in FIG. 5 is displayed.

FIGS. 1 to 6 relates to a first embodiment of the present invention. FIG. 1 is a view illustrating the entire configuration of an endoscope apparatus. FIG. 2 is a sectional view of an end portion of an endoscope. FIG. 3 is a front view of the end portion of the endoscope. FIG. 4 is a side view showing a hood member removably connected to the end portion of the endoscope. FIG. 5 is a plan view showing an observed image displayed on a monitor. FIG. 6 is a view illustrating an observing view area used if the observed image in FIG. 5 is displayed.

FIG. 1 shows the entire configuration of the endoscope apparatus.

As shown in FIG. 1, the endoscope apparatus 1 is composed of an endoscope 2, a light source device 3, a video processor 5, and a monitor 6.

The endoscope 2 comprises image pickup means described later. The light source device 3 is removably connected to the endoscope 2 to supply illumination light to a light guide formed in the endoscope 2. The video processor 5 is connected to the endoscope 2 via a signal cable 4 to control the image pickup means of the endoscope 2 and to process signals obtained from the image pickup means. The monitor 6 displays a video corresponding to an image of a subject output by the video processor 5.

The endoscope 2 has an inserted portion 7, a manipulating section 8, a connection cord 9, a connector section 10, and an electric connector section 11.

The inserted portion 7 is flexible and is formed to be elongated. The manipulating section 8 is connected to a proximal side of the inserted portion 7. The connection cord 9 is flexible and extends from a side of the manipulating section 8. The connector section 10 is provided at an end of the connection cord 9 and is adapted to be removably connected to the light source device 3. The electric connector section 11 is provided on a side of the connector section 10 so that the signal cable 4, connected to the video processor 5, can be removably connected to the electric connector section 11.

The electric connector section 11 is provided with a ventilation section (not shown) that allows the interior and exterior of the endoscope 2 to communicate with each other.

The connection between the inserted portion 7 and the manipulating section 8 is provided with an inserted-portion fold preventing member 12 having an elastic portion that prevents the connection from being sharply bent. The connection between the manipulating section 8 and the connection cord 9 is provided with a manipulating-section fold preventing member 13 similar to the inserted-portion fold preventing member 12. Furthermore, the connection between the connection cord 9 and the connector section 10 is provided with a connector-section fold preventing member 14 similar to the inserted-portion fold preventing member 12.

The inserted portion 7 is composed of a flexible tube portion 15, a bent portion 16, and an end portion 17 which are connected together in this order from the proximal end of the inserted portion.

The flexible tube portion 15 is formed so as to be flexible. The bent portion 16 is provided at the end of the flexible and can be bent while being manipulated by the manipulating section 8. An observing optical system, an illuminating optical system, and the like are disposed in the end portion 17; the optical systems are provided at the end of the inserted portion and will be described later.

As shown in FIGS. 2 and 3, the end portion 17 is provided with an air and water supply nozzle 18 as an air and water supply port, a suction port 19, a water supply port 20, an observing optical system 34, and an illuminating optical system 35.

The air and water supply nozzle 18 ejects a cleaning fluid or a gas to an optical member provided on an outer surface of the observing optical system 34. The suction port 19 is an opening located at the end of a treatment instrument channel through which a treatment instrument disposed in the inserted portion 7 is inserted or a liquid in the coelom is sucked. The water supply port 20 is open toward an object to be observed so that a liquid can be ejected to the object.

As shown in FIG. 1, the connector section 10 is provided with a gas supply cap 21, a water supply tank pressurizing cap 23, a water supply cap 24, a suction cap 25, an injection cap 26, and an earth terminal cap 27.

The gas supply cap 21 is removably connected to a gas supply source (not shown) built into the light source device. The water supply tank pressurizing cap 23 and the water supply cap 24 are removably connected to the water supply tank 22 as a water supply source. The suction cap 25 is connected to a suction source (not shown) to suck a gas or liquid through the suction port 19, shown in FIG. 3. The injection cap 26 is connected to water supply means (not shown) to feed water through the water supply port 20, shown in FIG. 3. The earth terminal cap 27 returns, to a high-frequency processor, a high-frequency leakage current generated in the endoscope 2 because of a high-frequency treatment or the like.

The manipulating section 8 is provided with an air and water supplying operation button 28, a sucking operation button 29, a bending operation knob 30, a plurality of remote switches 31, and a treatment instrument insertion port 32.

The air and water supplying operation button 28 is an operation section used to perform an air or water supplying operation. An operator can depress this button to supply air or liquid through the air and water supply nozzle 18, shown in FIG. 3. The sucking operation button 29 is an operation section used to perform a sucking operation. The operator can depress this button to perform a sucking operation through the suction port 19, shown in FIG. 3. The bending operation knob 30 is an operation section used to bend the bent portion 16. The plurality of remote switches 31 constitute an operation section used to remotely operate the video processor 5. The operation instrument insertion port 32 is a proximate opening that is in communication with the treatment instrument channel.

Further, a waterproof cap 33 can be removably connected to the electric connector section 11 of the endoscope 2 to seal the electric connector section 11 in a liquid tight manner.

Now, a hood member 37, an essential part of the present invention, will be described.

As shown in FIGS. 2 and 3, the hood member 37 is removably connected to the end portion 17 of the inserted portion 7 of the endoscope 2.

That is, the hood member 37, while fixed to the end portion 17, prevents a tip lens of the observing optical system 34 from directly abutting against the inner wall of the coelom. The hood member 37 thus prevents the view of the endoscope 2 from being blocked.

The hood member 37 can be formed of a soft member such as vulcanized rubber such as silicon rubber or fluorine rubber, or a thermoplastic elastomer such as an urethane-based elastomer, an acrylic-based elastomer, or an olefin based elastomer, or a hard resin such as polysulfon. In this embodiment, the hood member 37 is formed of the soft member.

The hood member 37 has a projecting portion 38 and an endoscope fixing portion 39.

The projecting portion 38 is shaped like a flower petal so as to project frontward in the view from the end portion 17. The endoscope fixing portion 39 is formed at a proximal end of the projecting portion 38 like a cylinder.

The endoscope fixing portion 39 is formed to have an inner diameter that is substantially the same as or slightly smaller than the outer diameter of the end portion 17. The endoscope fixing portion 39 is also formed to be deformable. Thus, the end portion 17 can be press-fitted into the endoscope fixing portion 39.

The endoscope fixing portion 39 is provided with a tapered portion 45 around the outer periphery of its proximal end portion. When the proximal end portion is formed like a low step and is made thin so as to be easily deformed, the tapered portion 45 allows the end portion 17 to be press-fitted into the endoscope fixing portion 39.

The level of clamping for press fitting is set to provide such a fixing strength that the hood member does not slip out in spite of the friction between itself and the wall of the coelom during examinations but can be easily removed after the operation has been completed. Specifically, it is set so that the amount of force required to remove the hood member is about 5 to 20 N.

The endoscope fixing portion 39 has as large a length as possible to the extent that the end of the endoscope fixing portion 39 does not reach the position of a rotationally moving pin 36 located at the tip of the bent portion 16. Thus, the endoscope fixing portion 39 is reliably fixed by maximizing the length over which the endoscope fixing portion 39 is fitted over the end portion 17 to the extent that a bending operation of the bent portion 16 is not affected. An end portion abutting portion 40 is formed between the endoscope fixing portion 39 and the projecting portion 38 so as to project from this position in such a manner that the diameter of the hood member at this position is smaller than the outer diameter of the end portion 17.

The end surface of the end portion 17 abuts against the end portion abutting portion 40 so as to position the end portion 17 and the hood member 37 in an axial direction. The end portion abutting portion 40 need not extend all over the circumference but over only part of it.

As shown in FIG. 3, the end portion abutting portion 40 is partly provided with a rotating direction positioning portion 41 projecting inward.

A concave nozzle engaging groove 42 is cut in the rotating direction positioning portion 41. The air and water supply nozzle 18 engages with the nozzle engaging groove 42 to position the end portion 17 and the hood member 37 in the direction of rotation around the axial direction.

The projecting portion 38 has a conical slope portion 44 formed on its inner peripheral surface and having a diameter increasing from the end portion abutting portion 40 to the end of the projecting portion. Thus, on the inner peripheral surface of the projecting portion 38, water, body fluids, contaminants, and other substances sticking to the surface of the end portion 17 are likely to flow easily to the exterior of the projecting portion 38. That is, the water and other substances are unlikely to remain there.

As shown in FIGS. 3 and 4, an edge portion 43 of the projecting portion 38 is shaped to correspond to an observation view area of the observing optical system 34 so as to minimize the area of that part of the end portion 43 which is viewed in an observed image.

As shown in FIG. 5, an observed image displayed on the monitor 6 is generally shaped like a rectangle.

FIG. 6 shows the observation view area used to display the observed image 46.

A face A1 is a lens face of the tip lens of the observing optical system 34, shown in FIG. 3. A face B1 is a virtual face located about 4 mm frontward from this lens face.

The observation view area on the face A1 is an area a1. The observation view area on the face B1 is an area b1.

The space sandwiched between the area a1 and the area b1 is an observation view area 47.

In this case, a side face of the observation view area 47 is a slope 48 formed of a set of light beams.

As shown in FIG. 5, the length L1 of the observed image 46 in its side-to-side direction is larger than its length L2 in its diagonal direction. Accordingly, the view angle is larger in the diagonal direction.

Further, with the observing optical system 34, typically used for the endoscope 2, owing to possible aberration based on its characteristics, an image is more markedly compressed at a position further from its center.

Thus, in the case of the shape of the observed image 46 shown in FIG. 5, the area b1 does not the same shape as the observed image 46 but is larger than the observed image 46 in the diagonal direction X, as shown in FIG. 6. Thus, the slope 48 has a biased shape.

As shown in FIGS. 2 and 4, the end edge portion 43 is shaped so as to correspond to the slope 48. A slope portion 49 shaped to have substantially the same shape as the slope 48, shown in FIG. 6, is formed on the end edge portion 43, shown in the upper part of FIGS. 2 and 4, and a portion 43a, shown shaded in FIG. 3, at the corresponding positions. Alternatively, as shown in FIGS. 2 and 4, the slope portion 49 is formed at positions slightly offset from the shape of the slope 48.

As shown in FIGS. 3 and 4, the end edge portion 43 is formed to be uneven so as to reflect the shape of the slope 48, described previously. In this case, in the end edge portion 43, portions A, B, C, and D are convex, while portions E, F, G, and H are concave.

If the projecting portion 38 includes a concave and convex portions, its part located near the observing optical system 34 is desirably shaped as a convex portion so as to have a larger projecting length. It is desirable to have at least three convex portions.

The portions E, F, G, and H, which are concave, are open outward because the slope portion 44 is connected to the slope 48. Mucus, contaminants, water supplied through the air and water supply nozzle, and the like are discharged from these concave portions to the exterior of the projecting portion 38 via the slope portion 44. This prevents contaminants, mucus, or the like from blocking the view.

As shown in FIG. 4, the end edge portion 43 has a chamfer 71 of R about 0.3 to 1 mm formed at its outer peripheral edge. The slope portion 49 also has a chamber of R about 0.3 to 1 mm formed at its end.

As shown in FIG. 2, the observing optical system 34 has an observation depth set between 4 and 100 mm. Further, the amount of projection L0 of the end edge portion 43 at the position at which it projects furthest from the tip lens of the observing optical system 34 is set to be substantially equal to or larger than the minimum value (near point) of this depth. In this embodiment, the end edge portion 43 is formed to project so that the amount of projection L0 is about 4 mm.

With this structure, the endoscope apparatus 1 of this embodiment is provided with the hood member 37 having the projecting portion 38 which is provided at the end portion 17 of the inserted portion 7 of the endoscope 2 and which projects in the direction of the observation view of the endoscope 2. The observed image 46, obtained through the endoscope 2, is not circular.

Further, in the endoscope apparatus 1, the projecting portion 38 has the slope portion 49 formed at its end edge potion 43 so as to correspond to the observation view area 47 of the endoscope 2.

If the hood member is transparent, it does not block illumination light. This results in high illumination performance.

The hood member may be black. In this case, the projecting portion may be aligned with the observation view area 47 of the endoscope 2. Further, like the previously described observing view are, the projecting portion may be provided with a notch and a slope portion.

If the hood member is black, illumination light is not reflected by the inner wall of the hood member. This prevents halation, which may occur when the treatment instrument is used.

Further, endoscopes applicable to the hood member may have the same color as the hood member, whereas endoscopes not applicable to the hood member may have a different color. Further, to allow the hood member to be easily removed from the end portion, the hood member and the end member may have different colors so as to be easily distinguished from each other.

The hood member may have the types of applicable endoscopes or the outer diameters of the end portions of these endoscopes indicated thereon.

The amount of projection of the projecting portion may be set between about 2 and 10 mm.

Figure 7:
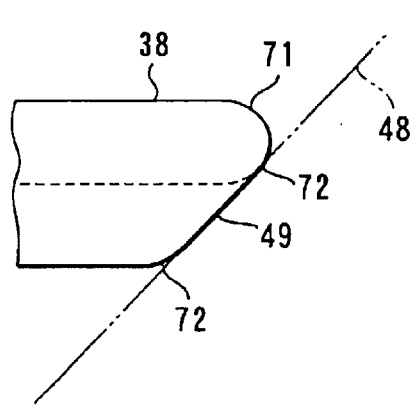
FIG. 7 is a first view illustrating effects of a projecting portion according to the first embodiment of the present invention.
Figure 8:
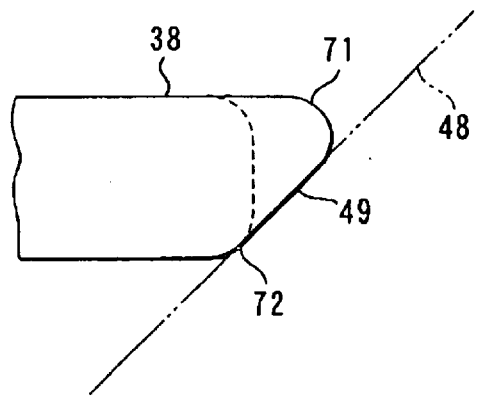
FIG. 8 is a second view illustrating effects of the projecting portion according to the first embodiment of the present invention.

FIGS. 7 and 8 are views illustrating effects of the projecting portion 38 according to the first embodiment. In FIG. 7, the solid line indicates the shape of the projecting portion 38 according to this embodiment. The broken line indicates the shape of the projecting portion 38 obtained if chamfers 71 and 72 are formed with the projecting length of the projecting portion 38 maintained and without providing the slope portion 49. If the projecting portion 38 is formed as shown by the broken line, the projecting portion 38 is thinner.

That is, in this embodiment, the slope portion 49 is formed to correspond to the observation view area 48, thereby increasing the thickness of the projecting portion 38 without reducing the projecting length of the projecting member 38. Thus, this embodiment makes the projecting portion 38 difficult to damage and prevents the projecting portion 38 from being deformed when pressed against the inner wall of the coelom even when it has a plurality of notches. Further, in this embodiment, the chamfers 71 and 72 may be formed to be large to allow the end portion to be easily inserted.

In FIG. 8, the solid line indicates the shape of the projecting portion 38 according to this embodiment. Further, the broken line indicates the shape of the projecting portion 38 obtained if it does not have the slope portion 49 formed thereon so as to have an adequate thickness. If the projecting portion 38 is formed as shown by the broken line, it has an insufficient projecting length.

That is, this embodiment enables the projecting length of the projecting portion 38 to be increased without increasing its outer diameter. This helps to improve the performance of the hood.

Further, even if the mucous membrane abuts against the end edge portion 43 to cover the entire view, the observing optical system 34 is focused on the mucous membrane on the end edge portion 43 by setting the amount of projection L0 of the end edge portion 43, shown in FIG. 2, to be larger than the value for the near point of the observation depth of the observing optical system 34. This makes the observed image clearer.

As described above, according to this embodiment, an endoscope apparatus can be provided which has a small diameter and in which the hood member 37 is difficult to damage, the endoscope apparatus allowing the ending end portion to be easily inserted into the hood member and serving to reduce the area of that part of the hood member 37 which is viewed in the observed image, thereby achieving high observation performance. Further, according to this embodiment, an endoscope apparatus is provided which exhibits high observation performance even if the hood member 37 abuts against the mucous membrane.

In the embodiment shown in FIGS. 1 to 6, an index used to position the hood member 37 in the rotating direction may be provided, for example, at the end edge potion 43 rather than forming the nozzle engaging groove 42. In this case, an index may be provided at the end portion 17, which is aligned with the index of the end edge portion 43, or the air and water supply nozzle 18, suction port 19, or observing optical system 34 of the end portion 17 may be aligned therewith.

If the hood member 37 is separate from the endoscope 2, the mounting position of the hood member 37 and the viewing of the observed image are likely to vary. However, a large protruding length is ensured in spite of such a variation by providing a slope portion corresponding to the observation view area at the respective positions to form as large a protruding length as possible.

Further, according to this embodiment, the hood member 37 can be easily mounted by providing positioning means for the axial or rotating direction or indices to arrange the slope portion at the appropriate position for the observation view area.

(Second Embodiment)

Figure 9:
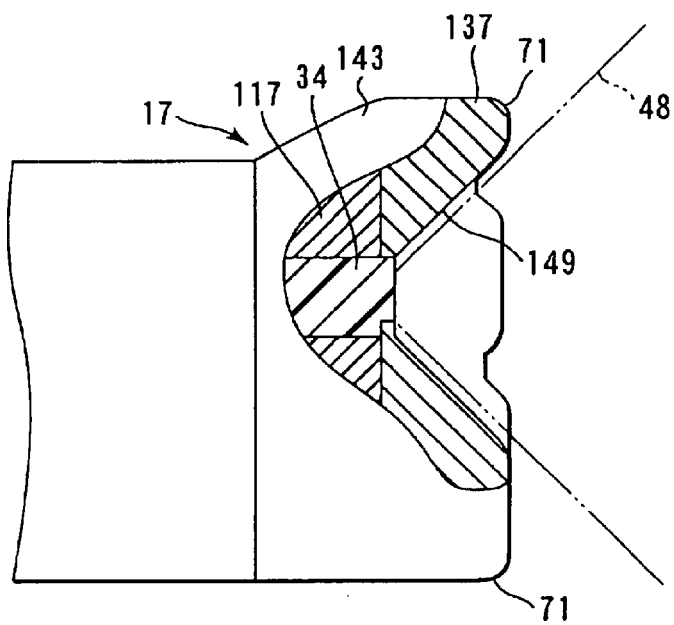
FIG. 9 is a partly cutaway side view of an end portion of an endoscope according to a second embodiment of the present invention.

FIG. 9 is a partly cutaway side view of an end portion of an endoscope according to a second embodiment of the present invention.

The second embodiment shown in FIG. 9 differs from the first embodiment in that a hood member 137 is integrated with the end portion 17.

As shown in FIG. 9, the hood member 137 is formed of a hard resin such as polysulfon and also acts as an insulating cover that covers a metal part inside the end portion 17.

The observing optical system 34 of the end portion 17 has an observation view area 47 similar to that in the first embodiment, shown in FIG. 6.

An end edge portion 143 of the hood member 137 has slope portions 149 formed at the respective positions and corresponding to the slope 48 of the observation view area 47.

The slope portion 149 is formed in the end edge portion 143 of the hood member 137 and corresponds to the slope 48 of the observation view area 47 at the respective positions as in the case with the first embodiment, shown in FIGS. 1 to 6.

Further, the end edge portion 143 has the chamfer 71 of R about 1 mm formed at its outer peripheral edge.

In this embodiment, the slope portion is formed to be as wide as possible, and the end edge portion 143 is formed to be as thick as possible.

If the hood member 137 and the end portion 17 are integrated together, a hard member is more durable than a soft member in terms of tearing and wearing.

If the hood member 137 is formed of a hard member, the end edge portion 143 is easier to damage when undergoing impact or the like compared to a soft member. However, in the second embodiment, the end edge portion 143 can be formed to be thick and the chamfer 71 can be formed to be markedly curved, thereby making the end edge portion 143 sufficiently difficult to damage even if the hood member 137 is hard.

(Third Embodiment)

Figure 10:
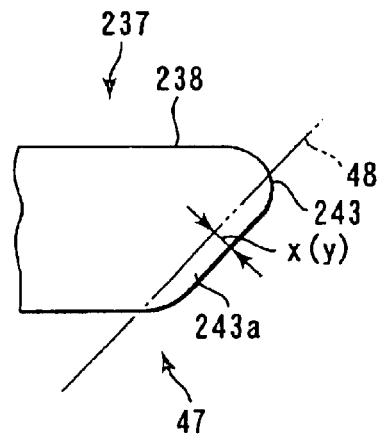
FIG. 10 is a side view showing a projecting portion of an end portion of an endoscope according to a third embodiment of the present invention.
Figure 11:
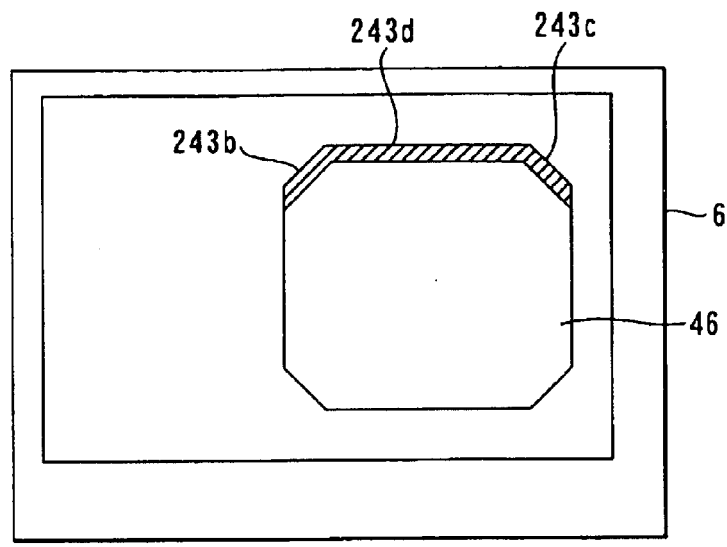
FIG. 11 a plan view showing an observed image displayed on a monitor according to the third embodiment of the present invention.

FIGS. 10 and 11 relate to a third embodiment of the present invention. FIG. 10 is a side view showing a protruding portion of the endoscope. FIG. 11 is a plan view showing an observed image displayed on a monitor.

As shown in FIG. 10, a protruding portion 238 of a hood member 237 provided at an end portion of the endoscope of this embodiment has a portion 243a formed so that a very small part of the end portion of the end edge portion 243 overlaps the slope 48 of the observation view area 47. That is, the portion 243a extends into the observation view area 47.

The amount of overlapping x by which the end edge portion 243 overlaps the observation view area 47 at positions distant from the center of the observation view area in the diagonal direction X shown in FIG. 6 is larger than the amount of overlapping y at other positions. That is, as shown in FIG. 11, considering aberration in the observing optical system 34, the amounts of overlapping x and y are set so that the area of that part of the end edge portion which is viewed on the observed image 46 is uniform.

In this embodiment, aberration in the observing optical system 34 causes the image to be most significantly compressed at positions distant from the center of the observation view area in the diagonal direction X shown in FIG. 6. Thus, as shown in FIG. 11, in the observed image 46 on the monitor 6, images 243b and 243c of the end edge portion 243 are compressed which project outward from the slope 48 in the diagonal direction X to overlap the observation view area 47. Thus, the images 243b and 243c of the end edge portion 243 are viewed on the observed image in substantially the same manner as an image 243d of the end edge portion 243 that overlaps the observation view area at other positions.

Thus, the protruding length or thickness of the hood member 237 can be formed to be large while minimizing the adverse effects on the observation view.

As described above, this embodiment produces effects similar to those of the embodiment shown in FIGS. 1 to 6. Furthermore, this embodiment provides an endoscope apparatus that allows the hood member 237 to be formed to have a large protruding length or thickness to allow the end portion to be easily inserted into the hood member for improved durability.

(Fourth Embodiment)

Figure 12:
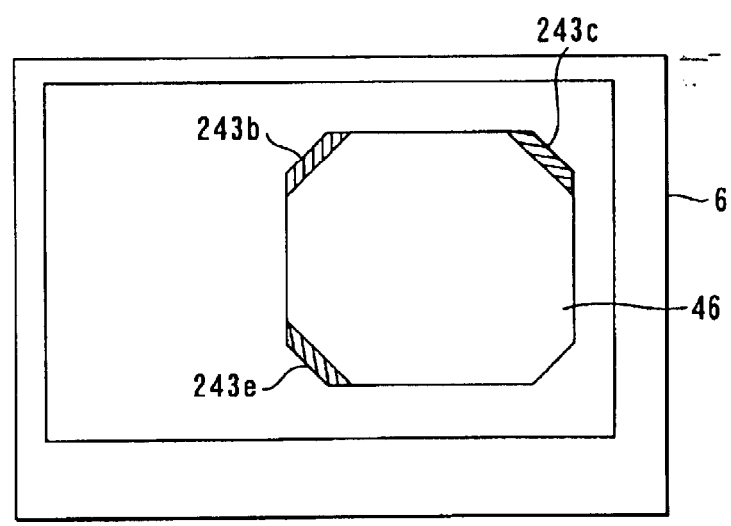
FIG. 12 a plan view showing an observed image displayed on a monitor of an endoscope apparatus according to a fourth embodiment of the present invention.

FIG. 12 is a plan view showing an observed image displayed on the monitor according to a fourth embodiment of the present invention. With reference to FIG. 10, description will be give of the shape of a protruding portion of an end portion of an endoscope according to the fourth embodiment.

This embodiment has a portion in which the end portion of the end edge portion 243 overlaps the slope 48 of the observation view area 47, shown in FIG. 10, by a very small amount only at positions distant from the center of the observation view area in the diagonal direction X. Thus, as shown in FIG. 12, the observed image 46 on the monitor 6 shows images 243b, 243c, and 243e of the end edge portion 243 which project outward from the slope 48 in the diagonal direction X to overlap the observation view area 47.

In this embodiment, that part of the view in the diagonal direction X which is significantly compressed and which has a large angle of view has a slightly reduced size in the observed image 46 on the monitor 6. However, the hood member 237 can be formed to have a large protruding length or thickness without further reducing the size of that part of the view which is insignificantly compressed and which originally has a small angle of view.

As described above, the fourth embodiment produces effects similar to those of the third embodiment, shown in FIGS. 10 and 11. Furthermore, the fourth embodiment provides an endoscope apparatus that exhibits high observation performance.

The first to fourth embodiments are applicable to endoscopes having circular observed images such as those shown in FIGS. 13, 14, 15, and 16.

Figure 13:
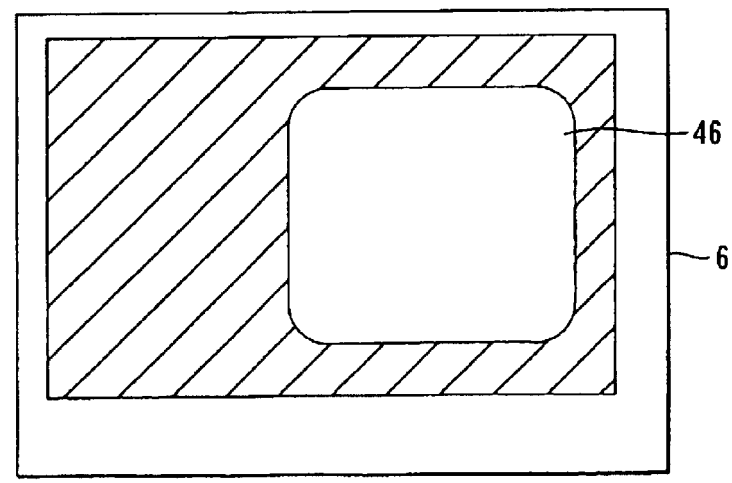
FIG. 13 is a plan view showing a first example of an observed image displayed on a monitor which can be used in the first to fourth embodiments.
Figure 14:
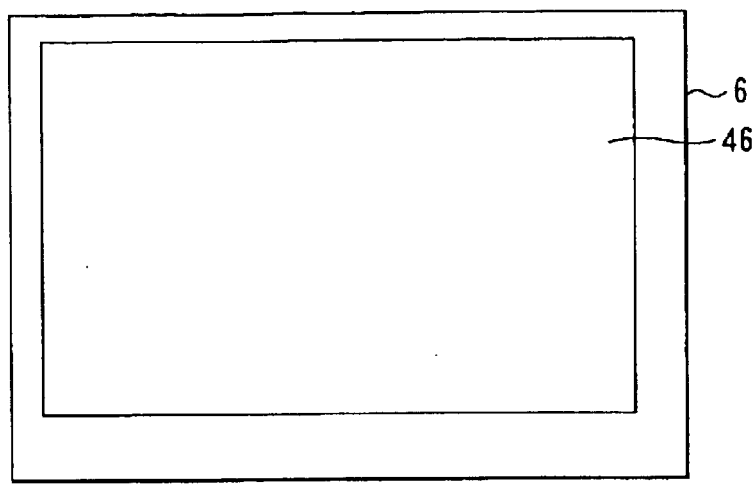
FIG. 14 is a plan view showing a second example of an observed image displayed on the monitor which can be used in the first to fourth embodiments.
Figure 15:
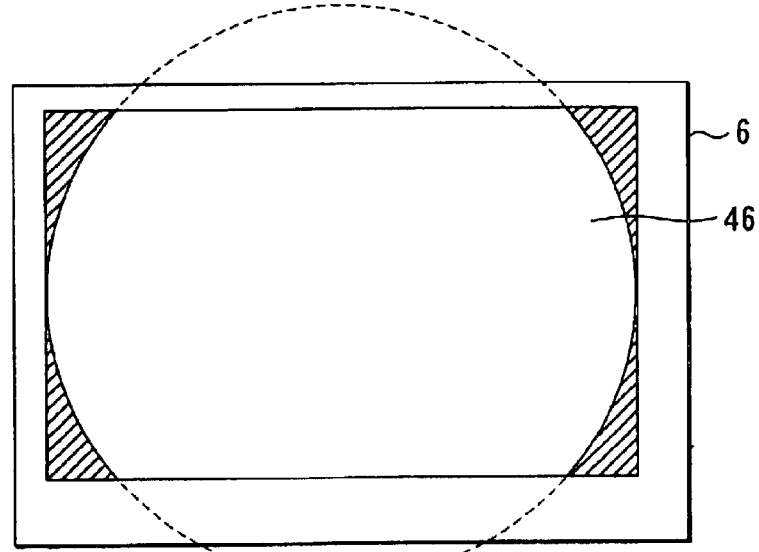
FIG. 15 is a plan view showing a third example of an observed image displayed on the monitor which can be used in the first to fourth embodiments.
Figure 16:
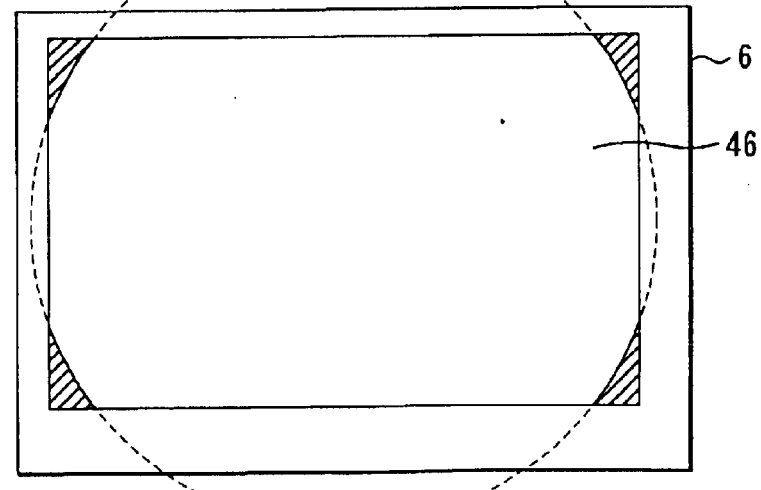
FIG. 16 is a plan view showing a fourth example of an observed image displayed on the monitor which can be used in the first to fourth embodiments.

In FIG. 13, the observed image 46 is a general square or rectangle with rounded corners. In FIG. 14, the observed image 46 is a rectangle displayed all over the screen of the monitor 6. In FIG. 15, the observed image 16 is a general rectangle obtained by cutting out the top and bottom of a circle. In FIG. 16, the observed image 16 is a general rectangle obtained by cutting out the top, bottom, and rightmost and leftmost portions of a circle.

(Fifth Embodiment)

Figure 17:
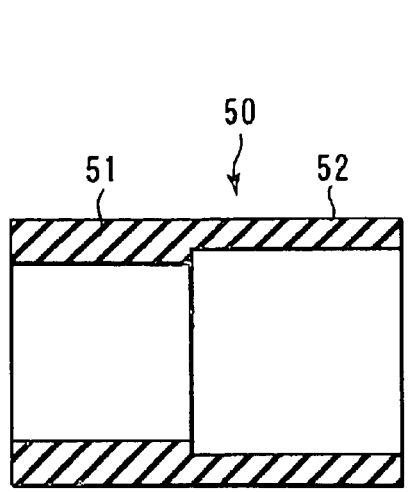
FIG. 17 is a sectional view showing a hood member used for a fitting jig according to a fifth embodiment of the present invention.
Figure 18:
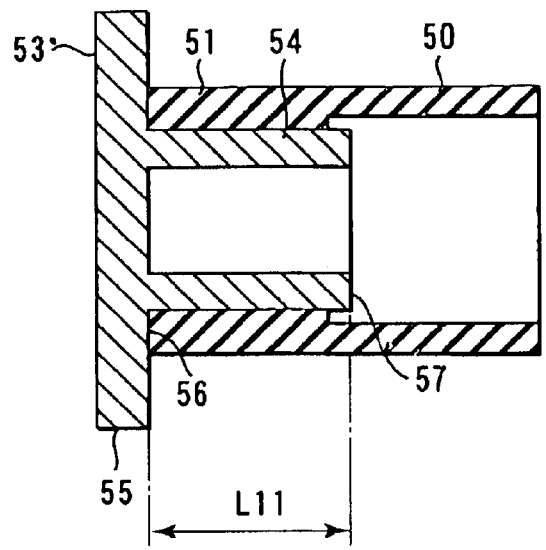
FIG. 18 is a sectional view showing the hood member fitting jig according to the fifth embodiment of the present invention.
Figure 19:
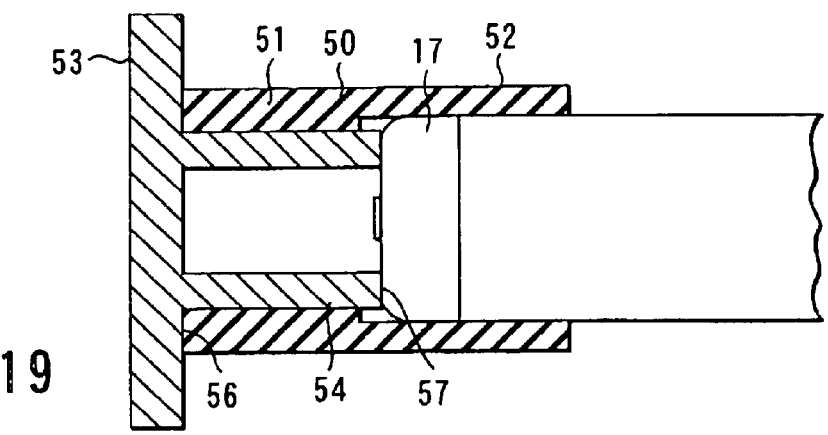
FIG. 19 is a sectional view showing how the hood member is fitted over an end portion of an endoscope using the hood member fitting jig in FIG. 18.
Figure 20:
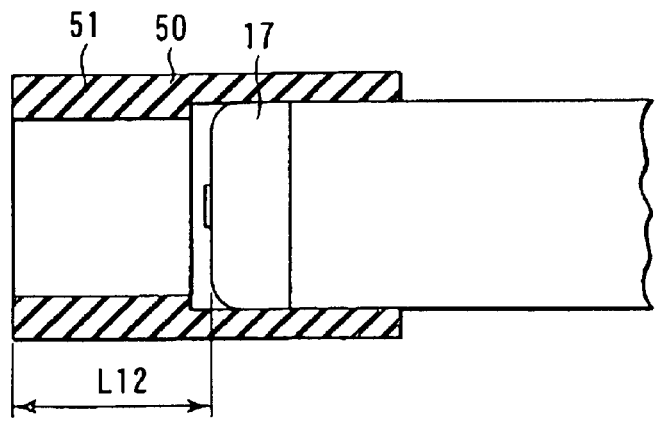
FIG. 20 is a sectional view showing that the hood member fitting jig shown in FIG. 19 has been removed.

FIGS. 17 to 20 relate to a fifth embodiment of the present invention. FIG. 17 is a sectional view showing a hood member. FIG. 18 is a sectional view showing a hood member fitting jig in which the hood member has been fitted. FIG. 19 is a sectional view showing how the hood member is fitted over an end portion of an endoscope using the hood member fitting jig in FIG. 18. FIG. 20 is a sectional view showing that the hood member fitting jig shown in FIG. 19 has been removed.

As shown in FIG. 17, a hood member 50 is generally cylindrical and can be fitted over and removed from the end portion of the endoscope. The hood member 50 can be formed of a soft member such as vulcanized rubber such as silicon rubber or fluorine rubber, or a thermoplastic elastomer such as an urethane-based elastomer, an acrylic-based elastomer, or an olefin-based elastomer, or a hard resin such as polysulfon. In this embodiment, the hood member 50 is formed of the soft member.

The hood member 50 has a projecting portion 51 and an endoscope fixing portion 52.

The endoscope fixing portion 52 of the hood member 50 is formed to have an inner diameter that is substantially the same as or slightly smaller than the outer diameter of the end portion 17 of the endoscope shown in FIG. 19. Thus, the end portion 17 can be press-fitted into the endoscope fixing portion 52 owing to elastic deformation.

As shown in FIG. 18, a hood member fitting jig 53 is used to allow the removable hood member 50 to be fitted over the end portion 17 of the endoscope shown in FIG. 19.

The hood member fitting jig 53 is provided with a hood member fixing portion 54 and a gripped portion 55.

The hood member fixing portion 54 is formed to have an outer diameter substantially the same as the inner diameter of the protruding portion 51.

The hood member fixing portion 54 has a hood member abutting portion 56 formed at its proximal end portion. The hood member fixing portion 54 has an end portion abutting portion 57 formed at its end.

The length L11 between the hood member abutting portion 56 and the end portion abutting portion 57 is equal to the optimum amount of projection L12 of the protruding portion 51 from the end portion 17 with which the area of that part of the hood member 50 which is viewed in the observation area is permissible when the hood member 50 is fitted over the end portion 17 and with which the hood member 50, shown in FIG. 20, produces maximum effects.

With this structure, the hood member abutting portion 56 acts as hood member regulating means for regulating the position of the hood member 50. The end abutting portion 57 acts as end regulating means for regulating the position of the end portion 17. When the hood member 50 is fitted over the end portion, the hood member fitting jig 53 regulates the fitting position of the hood member 50 with respect to the end portion 17.

To fit the hood member 50 over the end portion 17, the hood member fixing portion 54 of the hood member fitting jig 53 is inserted into the projecting portion 51 of the hood member 50 until the hood member abutting portion 56 abuts against the end portion of the projecting portion 51, as shown in FIG. 18.

Then, as shown in FIG. 19, the end portion 17 is press-fitted into the endoscope fixing portion 52 of the hood member 50 and inserted therethrough until the end potion abutting portion 57 abuts against the end portion 17.

Once the end portion abutting portion 57 abuts against the end portion 17 and the hood member abutting portion 56 abuts against the end portion of the projecting portion 51, the hood member fitting jig 53 is removed from the hood member 50 as shown in FIG. 20.

Alternatively, the hood member may be fitted in the following order:

First, the end portion 17 is press-fitted into the endoscope fixing portion 52 of the hood member 50 by an appropriate amount. Subsequently, the hood member fixing portion 54 of the hood member fitting jig 53 is inserted into the projecting portion 51 of the hood member 50.

Then, the position of the hood member 50 is adjusted so that the hood member abutting portion 56 abuts against the end portion of the projecting portion 51, while the end portion abutting portion 57 abuts against the end portion 17. Subsequently, the hood member fitting jig 53 is removed.

Thus, as shown in FIG. 20, the hood member 50 is fixed to the end portion 17 by regulating its axial position so as to correspond to the appropriate amount of projection L12 with respect to the end portion 17.

As described above, according to the fifth embodiment, a hood member fitting jig 53 is provided which allows the hood member 50 to be reliably and easily installed in position by regulating the axial position of the hood member and which achieves high observation performance.

(Sixth Embodiment)

Figure 21A:
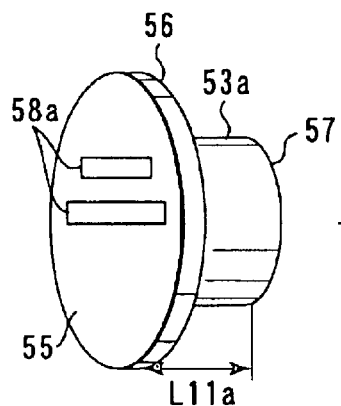
FIGS. 21A to 21C illustrate how a hood member is installed using a hood member fitting jig according to a sixth embodiment of the present invention.
Figure 21A:
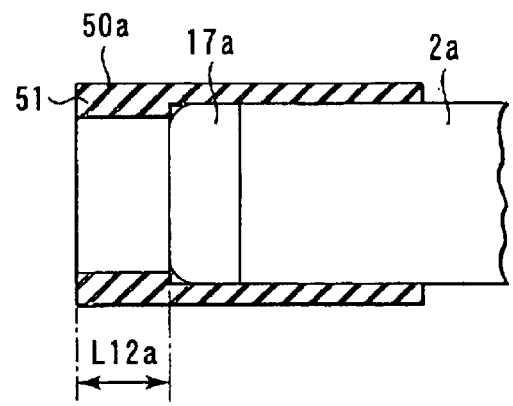
Figure 21B:
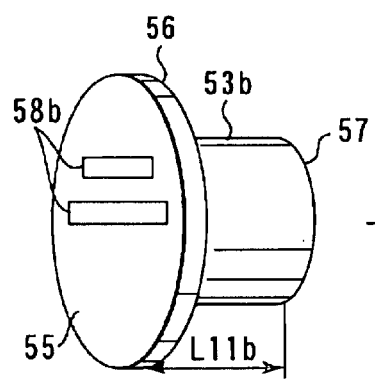
Figure 21B:
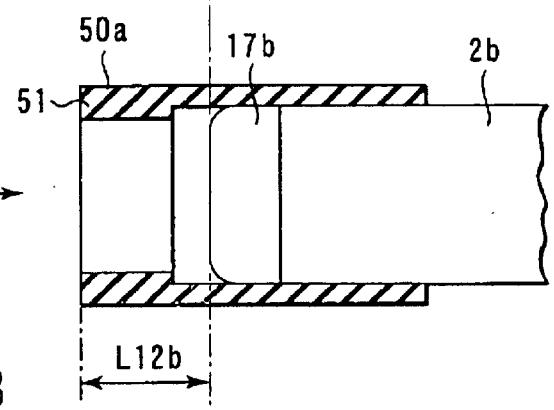
Figure 21C:
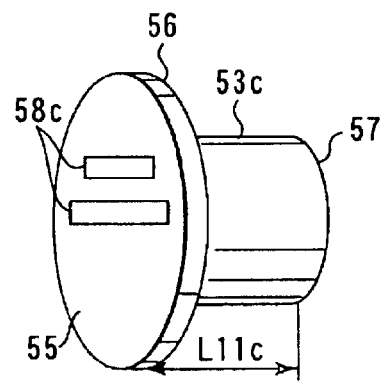
Figure 21C:
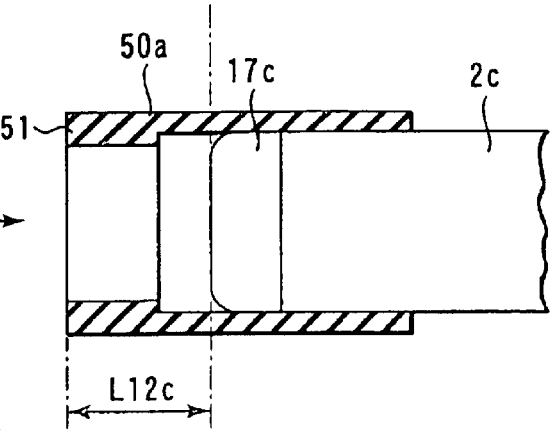

FIGS. 21A to 21C are views illustrating a method of fitting a hood using a hood member fitting jig according to a sixth embodiment of the present invention.

As shown in FIGS. 21A to 21C, three types of endoscopes 2a, 2b, and 2c have respective end potions 17a, 17b, and 17c which have substantially the same outer diameter.

On the other hand, the end portions 17a, 17b, and 17c each have the observing optical system 34, illuminating optical system 35, air and water supply nozzle 18, suction port 19, and others laid out in a manner different from that shown in FIG. 2.

Further, the observation view area for observed images displayed on the monitor 6, shown in FIG. 1, varies depending on differences in the configuration of lenses (not shown) constituting the observing optical system 34, differences in a CCD, differences in the display form of the observed image 46 on the monitor under the control of the video processor 5, and other differences.

Thus, when one type of hood member 50a is fitted over three types of end portions 17a, 17b, and 17c, if the projecting portion 51 projects from the end portion 17 by the same amount in each case, the area of that part of the hood member 50a which is viewed in the observed image may vary.

On the other hand, the hood member 50a can be used for all of the endoscopes 2a, 2b, and 2c.

The endoscopes 2a, 2b, and 2c have different optimum amounts of projection L12 with which the area of that part of the hood member 50 which is viewed in the observed image is permissible when the hood member 50 is fitted over the end portions 17a, 17b, and 17c and with which the hood member produces maximum effects.

When the hood member 50a is fitted over the endoscopes 2a, 2b, and 2c, exclusive hood member fitting jigs 53a, 53b, and 53c are used.

The lengths L11a, L11b, and L11c between the hood member abutting portions 56 of the hood member fitting jigs 53a, 53b, and 53c and the end portion abutting portion 57 are equal to the amounts of projection L12a, L12b, and L12c, respectively, as shown in FIGS. 21A to 21C.

The gripped portion 55 is provided with display portions 58a, 58b, and 58c that have the name and model number of each endoscope, the name and model number of the hood member 50a, the name of the manufacturer, and the like displayed thereon by molding or printing.

To install the hood member 50a, the displayed contents of the display portions 58a, 58b, and 58c are checked to select a hood member fitting jig corresponding to each endoscope.

The installation procedure is similar to that in the fifth embodiment, shown in FIG. 20.

With the endoscopes 2a, 2b, and 2c, the hood member 50a is fixed to the end portions 17a, 17b, and 17c by having its axial position regulated so as to correspond to the appropriate amounts of projection L12a, L12b, and L12c, respectively.

The sixth embodiment produces effects similar to those of the fifth embodiment, shown in FIGS. 17 to 20, and allows a common hood member to be installed at the optimum position in each of the end portions of the different endoscopes.

(Seventh Embodiment)

Figure 22:
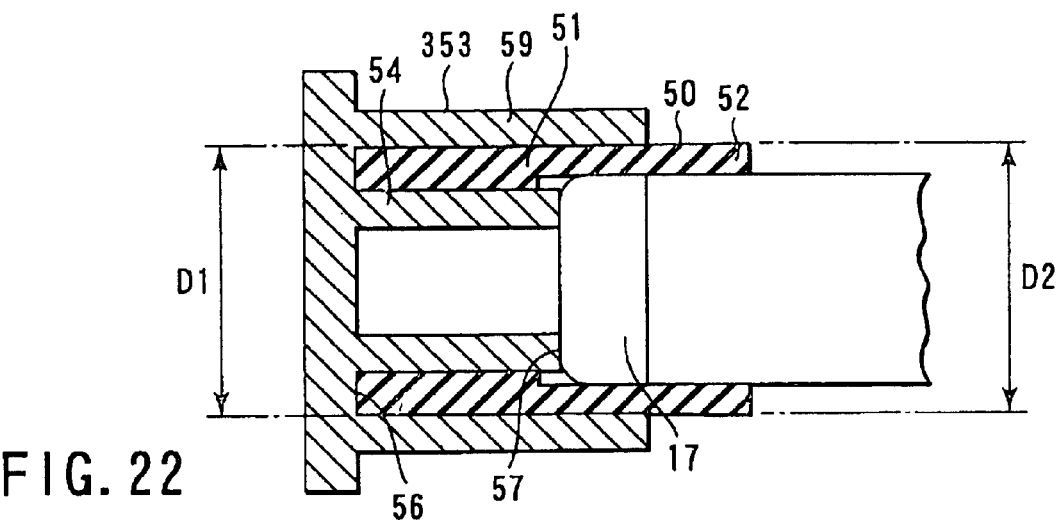
FIG. 22 is a sectional view showing that a hood member has been fitted over the end portion of the endoscope using a hood member fitting jig according to a seventh embodiment.

FIG. 22 is a sectional view showing that a hood member has been fitted over the end portion of the endoscope using a hood member fitting jig according to a seventh embodiment. In FIG. 22, components similar to those of the embodiment shown in FIG. 19 are denoted by the same reference numerals. Description of these components is omitted.

As shown in FIG. 22, a hood member fitting jig 353 is provided with an outer diameter regulating portion 59.

The outer diameter regulating portion 59 has an inner diameter D1 substantially the same as the outer diameter D2 of the projecting portion 51 of the hood member 50. Thus, the projecting portion 51 can be inserted into the outer diameter regulating portion 59.

To fit the hood member 50 in the hood member fitting jig 353, the projecting portion 51 of the hood member 50 is inserted between the hood member fixing portion 54 and the outer diameter regulating portion 59.

Then, as in the case with FIG. 19, the end portion 17 is press-fitted into the endoscope fixing portion 52 of the hood member 50. Subsequently, the hood member fitting jig 353 is removed from the hood member 50. Thus, as in the case with FIG. 20, the hood member 50 is fixedly mounted on the end portion 17.

Figure 23:
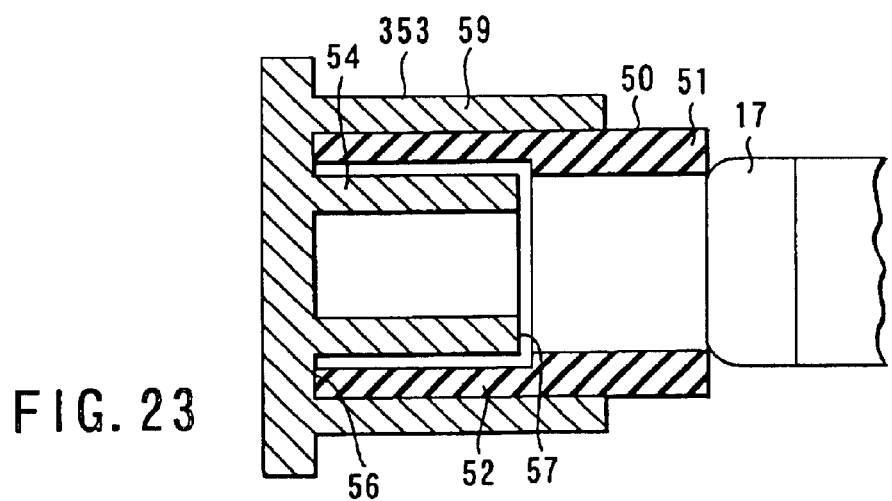
FIG. 23 is a view illustrating effects of the seventh embodiment in FIG. 22 produced if the hood member is mistakenly fitted in the hood member fitting jig in a side-to-side axial direction.

FIG. 23 is a view illustrating effects of this embodiment produced if the hood member 50 is mistakenly fitted in the hood member fitting jig 353 in a side-to-side axial direction and then an attempt is made to fit the hood member 50 over the end portion 17.

As shown in FIG. 23, the endoscope fixing portion 52 of the hood member 50 is inserted between the hood member fixing portion 54 and the outer diameter regulating portion 59 in the direction opposite to the correct one.

In this state, even if an attempt is made to press-fit the end portion 17 into the projecting portion 51 of the hood member 50, this attempt fails because the inner diameter of the projecting portion 51 is smaller than the inner diameter of the endoscope fixing portion 52 and the outer diameter of the end portion 17 and because the outer diameter regulating portion 59 regulates deformation of the protruding portion 51, thereby precluding the diameter of the projecting portion 51 from being increased.

This prevents the hood member 50 from being fitted over the end portion 17 in the direction opposite to the correct one.

Figure 24:
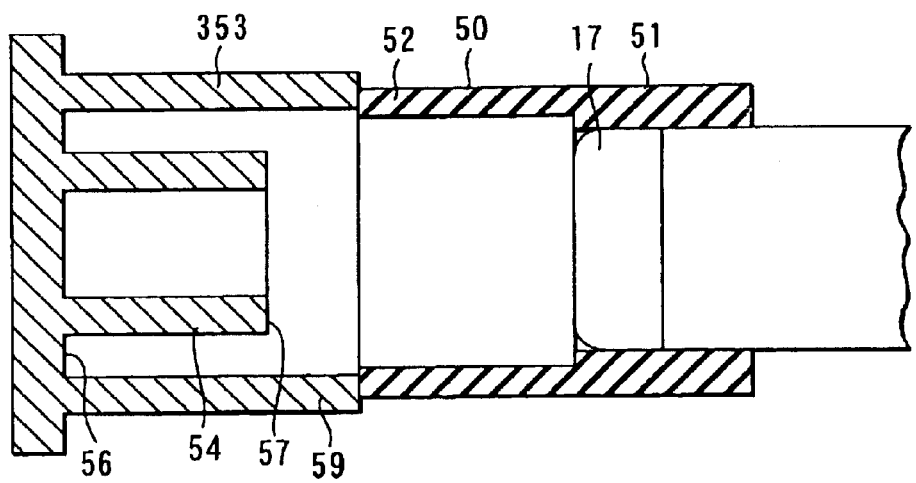
FIG. 24 is a view illustrating the effect of the seventh embodiment in FIG. 22 produced if the hood member is mistakenly fitted in the hood member fitting jig in the side-to-side axial direction.

FIG. 24 is a view illustrating effects of this embodiment in FIG. 22 produced if the hood member 50 is mistakenly first fitted over the end portion 17 in the side-to-side axial direction.

As shown in FIG. 24, the end portion 17 is press-fitted into the projecting portion 51 of the hood member 50 by an appropriate amount.

In this case, the inner diameter of the projecting portion 51 is not appropriate for the outer diameter of the end portion 17. However, the hood member 50 may be elastically deformed so as to increase its diameter and may thus be successfully fitted over the end portion 17.

Then, when an attempt is made to insert the hood member fixing portion 54 of the hood member fitting jig 353 into the endoscope fixing portion 52 of the hood member 50, the endoscope fixing portion 53 abuts against the outer diameter regulating portion 59 to preclude the insertion because the endoscope fixing portion 52 of the hood member 50 has been deformed so as to increase its diameter.

This prevents the hood member 50 from being fitted over the end portion 17 in the direction opposite to the correct one.

The seventh embodiment produces effects similar to those of the fifth embodiment, shown in FIGS. 17 to 20, and prevents the hood member from being mistakenly fitted in the side-to-side axial direction.

(Eighth Embodiment)

Figure 25:
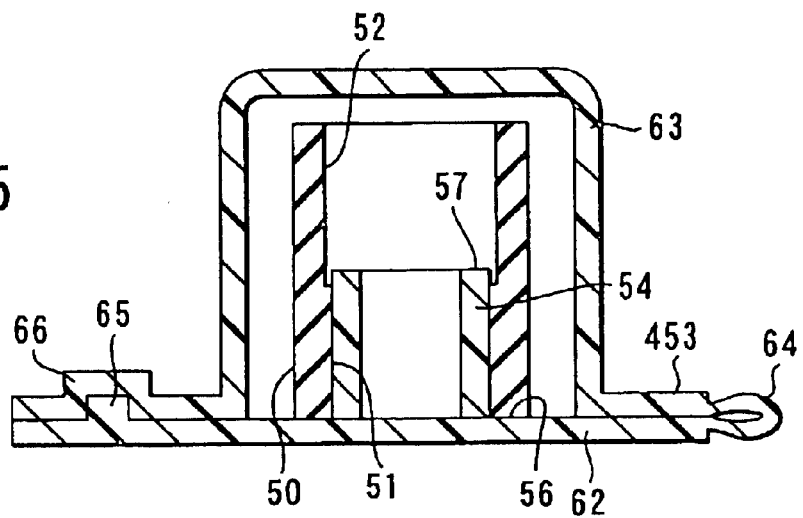
FIG. 25 is a sectional view showing a hood member fitting jig according to an eighth embodiment of the present invention.
Figure 26:
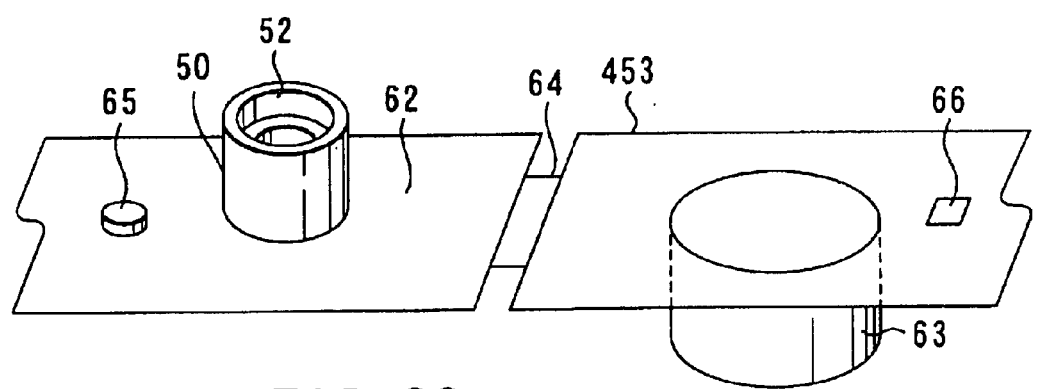
FIG. 26 is a perspective view showing that the hood member fitting jig in FIG. 25 has been opened.

FIGS. 25 and 26 relate to an eighth embodiment. FIG. 25 is a sectional view showing that a hood member fitting jig with a hood member mounted has been closed. FIG. 26 is a perspective view showing that the hood member fitting jig has been opened.

As shown in FIGS. 25 and 26, a hood member fitting jig 453 also acts as a package for the hood member 50.

The hood member fitting jig 453 has a main body portion 62, a cap-like accommodating portion 63, and a hinge portion 64 joining the main body portion 62 and the cap-like accommodating portion 63 together.

Further, the hood member fitting jig 453 is formed of a resin member that can be sterilized using an ethylene oxide gas, an autoclave, or gamma rays. For example, the hood member fitting jig 453 is formed of polyethylene, which can be sterilized using an ethylene oxide gas.

The main body portion 62 is provided with the hood member fixing portion 54, which is similar to that shown in FIG. 18 and to which the hood member 50 has already been fixed.

The hood member fixing portion 54 is formed to have an outer diameter slightly larger than the inner diameter of the projecting portion 51. The hood member fixing portion 54 has been press-fitted into the projecting portion 51. The projecting portion 51 is fixed to the hood member fixing portion 54 owing to its own elastic force. The outer diameter of the hood member fixing portion 54 is set so that the force required to fix the projecting portion 51 and the hood member fixing portion 54 together is weaker than the force required to fix together the endoscope fixing portion 52 and the end portion 17, shown in FIG. 19. Further, the main body portion 62 is provided with the hood member abutting portion 56 and end portion abutting portion 57, which are similar to those shown in FIG. 19.

The main body portion 62 has a convex portion 65 formed thereon. The accommodating portion 63 has a locking portion 66 formed thereon to removably lock the convex portion 65.

With the hood member fitting jig 453, the convex portion 65 engages with the locking portion 66 for locking to lock the main body portion 62 on the accommodating portion 63. This allows the hood member 50 to be accommodated as shown in FIG. 25.

The hood member fitting jig 453 can be sterilized as described above. The hood member fitting jig 453 is accommodated in a peel pack or the like which can keep its contents sterile for a specified period of time. Thus, while remaining sterile in this manner, the hood member fitting jig 453 is delivered to the user.

To fit the hood member 50 over the end portion 17, shown in FIG. 19, the peel pack is opened to remove the hood member fitting jig 453, shown in FIG. 25. Then, as shown in FIG. 26, the main body portion 62 is unlocked from the accommodating portion 63 to expose the hood member 50. The hood member fitting jig 453 still serves to keep the hood member 50 sterile.

Then, the end portion 17, shown in FIG. 19, is inserted into the endoscope fixing portion 52. Subsequently, as in the case with the fifth embodiment, the hood member 50 is positioned and fixed to the end portion 17, and the hood member fitting jig 453 is removed from the hood member 50. In this case, since the outer diameter of the hood member fixing portion 54 is set so that the force required to fix the projecting portion 51 and the hood member fixing portion 54 together is weaker than the force required to fix the endoscope fixing portion 52 and the end portion 17 together, the hood member fitting jig 453 can be removed from the hood member 50 without displacing the hood member 50 from the end portion 17, even if the hood member 50 is not gripped by the fingers.

As described above, the hood member 50 can be fitted over the end portion 17 without manually removing the hood member 50 from the hood member fitting jig 453 or touching the hood member 50.

The eighth embodiment produces effects similar to those of the fifth embodiment, and eliminates the need to mount the hood member on the hood member fitting jig before an examination. This further facilitates the installation. Further, the hood member is fixed to the hood member fitting jig beforehand, thereby preventing the hood member from being mistakenly installed in the side-to-side axial direction. Furthermore, the hood member can be kept clean until immediately before use.

(Ninth Embodiment)

Figure 27:
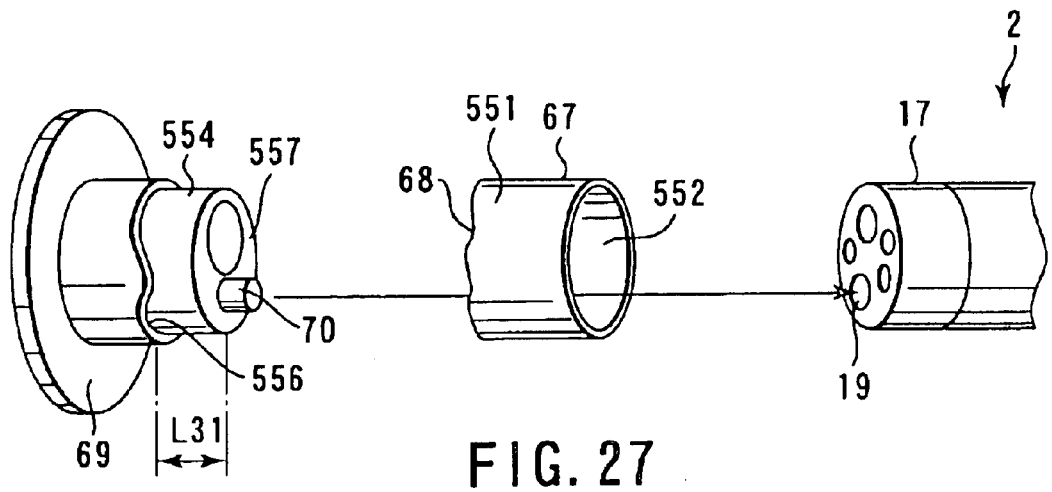
FIG. 27 is a view illustrating that a hood member is mounted on the end portion of the endoscope using a hood member fitting jig according to a ninth embodiment of the present invention.

FIG. 27 is a view illustrating that a hood member is mounted on the end portion of the endoscope using a hood member fitting jig according to a ninth embodiment of the present invention.

As shown in FIG. 27, the edge of an end abutting portion 68 located at the end of a projecting portion 551 of a hood member 67 is shaped like a flower petal so as to correspond to an observed image.

A hood member fixing portion 554 of a hood member fitting jig 69 has a hood member abutting portion 556 provided at its proximal end and having substantially the same shape as the end abutting portion 68.

The hood member fixing portion 554 has an end portion abutting portion 557 formed at its end. The hood member fixing portion 554 is provided with a cylindrical rotating-direction regulating portion 70 projecting from the end abutting portion 557.

The rotating-direction regulating portion 70 has an outer diameter substantially the same as the inner diameter of the suction port 19, formed in the end portion 17. Accordingly, the rotating-direction regulating portion 70 can be fitted into the suction port 19.

To fit the hood member 67 in the hood member fitting jig 69, the end abutting portion 68 of the hood member 67 is abutted against the hood member abutting portion 556, having substantially the same shape as the end abutting portion 68, so that the end abutting portion 68 is located so as to correspond to the hood member abutting portion 556. This allows the hood member 67 to be set at a predetermined position in the rotating direction with respect to the hood member fitting jig 69.

Then, the hood member fitting jig 69 and the end portion 17 are aligned with each other in the rotating direction so that the rotating-direction regulating portion 70 can be fitted into the suction port 19 of the endoscope 2. Then, the hood member 67 is fixed to the end portion 17 at the position where the end portion 17 abuts against the end abutting portion 557.

This allows the hood member abutting portion 556 to regulate the positions of the hood member 67 and hood member fitting jig 69 in the rotating direction and in the axial direction. On the other hand, the fitting of the end portion in the endoscope fitting portion 552 regulates their positions in the rotating direction; the fitting of the rotating-direction regulating portion 70 in the suction port 19 regulates their positions in the rotating direction.

As described above, the end abutting portion 68 is installed in a position so that its axial position is set so as to achieve an appropriate amount of projection L31 with respect to the end portion 17, while its position in the rotating direction is regulated so as to correspond to the observed image.

According to the ninth embodiment, a hood member fitting jig is provided which enables the end portion 17 to be reliably and easily installed in position by regulating the positions of the end abutting portion 68 in the axial and rotating directions and which achieves high observation performance.

The rotating-direction regulating portion 70 is configured to engage with the suction port 19 to regulate the positions in the rotating direction. However, the rotating-direction regulating portion 70 may be configured to engage with the air and water supply nozzle 18, which projects from the end surface of the end portion 17. Thus, the rotating-direction regulating portion may be configured to engage with a concave portion such as the suction port 19, formed at a position other than the center of the end surface of the end portion 17, or a convex portion such as the air and water supply nozzle 18.

This eliminates the need to form a regulating portion on an outer peripheral portion of the end portion 17, the regulating portion regulating the positions in the rotating direction. Accordingly, a new complicated regulating portion need not be formed, thereby reducing the diameter of the apparatus.

Further, the endoscope 2 need not have any new arrangements for positioning. Consequently, this embodiment is applicable to existing endoscopes 2 and can thus be used for various applications.

A concave or convex portion may be formed on the end portion 17 separately from the suction port 19 or the air and water supply nozzle 19. The hood member fitting jig 69 may be configured as with the eighth embodiment.

(Tenth Embodiment)

Figure 28:
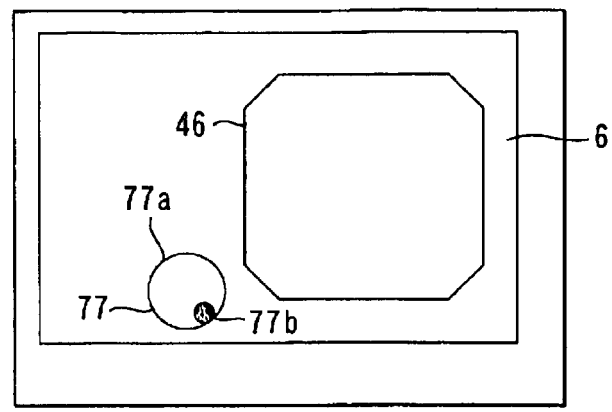
FIG. 28 is a plan view showing an observed image displayed on a monitor of an endoscope apparatus according to a tenth embodiment of the present invention.

FIG. 28 is a plan view showing an observed image displayed on a monitor of an endoscope apparatus according to a tenth embodiment of the present invention. The entire configuration of the endoscope apparatus, which is not shown in FIG. 28, will be described with reference to FIGS. 1 to 3.

As shown in FIG. 1, the endoscope apparatus 1 of the tenth embodiment has the endoscope 2 having the suction port 19 at the end portion of the inserted portion 7, and the video processor 5 acting as image display means for displaying an image picked up via the endoscope 2 on the monitor as an observed image 46.

The video processor 5 is provided with a display section 76 that displays, when the observed image 46 is displayed on the monitor 6, the position of the suction port 19 corresponding to the observed image 46 on the monitor 6.

More specifically, the endoscope 2 has storage means 75 provided inside the connector section 10 and composed of a nonvolatile memory such as an EEPROM or a flash ROM. The storage means 75 stores endoscope-specific information such as the model name of the endoscope 2 and the inner diameter of the previously described operation instrument channel. The storage means 75 also stores information on the position, in the end portion 17, of the suction port 19, i.e. an end-side opening of the treatment instrument channel. Furthermore, the storage means 75 is connected to the electric connector section 11 via a signal line (not shown) so as to form a circuit.

The video processor 5 is provided with a display section 76.

When the endoscope 2 and the video processor 5 are connected together via the signal cable 4, the storage means 75 and the display section 76 are connected together via a signal line (not shown) so as to form a circuit.

The display section 76 is configured to read the positional information on the suction port 19 stored in the storage means 75 and to provide a suction port display 77 based on symbols, characters, or the like near the observed image 46 on the monitor 6, the suction port display 77 indicating the position of the suction port 19 corresponding to the observed image 46, as shown in FIG. 28. In this embodiment, a large circle 77a indicates the end portion 17 of the endoscope 2, whereas a small circle 77b indicates the position of the suction port 19. FIG. 28 shows that the suction port 19 is located in the lower right of the end portion 17 in the direction in which the observed image 46 is observed.

During examinations, the suction port display 77 is provided near the observed image 46 on the monitor to indicate the position of the suction port 19 specific to this endoscope.

The operator can recognize the position of the suction port 19 on the basis of the suction port display 77 to determine that the suction port 19 is approaching the mucous membrane.

Thus, the operator can prevent a suction operation if the mucous membrane is likely to be sucked.

The tenth embodiment provides an endoscope apparatus which is unlikely to suck the mucous membrane, thereby reducing the number of operations of clearing the endoscope end portion of the mucous membrane, which has been sucked by the suction port 19, during insertion, observation, or operation. This improves workability.

Figure 29:
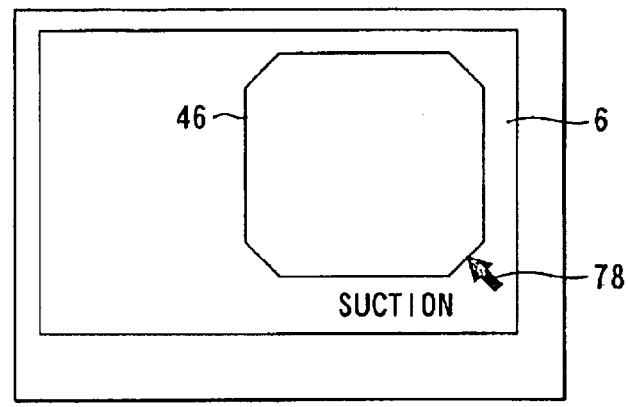
FIG. 29 is a plan view showing an observed image displayed on a monitor of an endoscope apparatus according to a variation of the tenth embodiment of the present invention.

FIG. 29 is a plan view showing an observed image displayed on a monitor of an endoscope apparatus according to a variation of the tenth embodiment of the present invention.

As shown in FIG. 29, this variation provides a suction port display 78 near the observed image 46 on the monitor 6 which indicates the direction in which the suction port 19 lies with respect to the observed image 46. The suction port display 78 indicates the direction of the suction port 19 using an arrow and characters.

During examinations, the suction port display 77 is provided near the observed image 46 on the monitor 6.

Such a variation produces effects similar to those of the tenth embodiment, shown in FIG. 28.

(Eleventh Embodiment)

Figure 30:
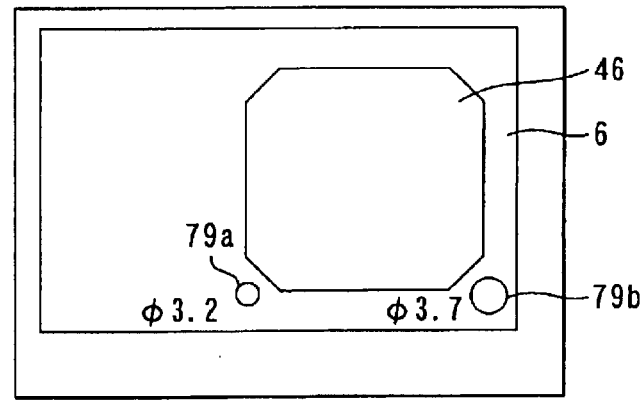
FIG. 30 is a plan view showing an observed image displayed on a monitor of an endoscope apparatus according to an eleventh embodiment of the present invention.

FIG. 30 is a plan view showing an observed image displayed on a monitor of an endoscope apparatus according to an eleventh embodiment of the present invention.

As shown in FIG. 30, in the eleventh embodiment of the present invention, the endoscope has two operation instrument channels.

These operation instrument channels are different.

The storage means stores the positions of the two suction ports as well as information on their diameters.

On the monitor 6, suction port displays 79a and 79b are provided near the observed image 46 to indicate the positions of the two suction ports corresponding to the observed image 46 as well as the difference in size between these ports. The circles of the suction ports 79a and 79b indicate the directions of the suction ports, and their sizes indicate the difference in diameter between the treatment instrument channels.

Further, the inner diameters of the treatment instrument channels are simultaneously indicated in letters.

The eleventh embodiment of the present invention produces the same effects as the tenth embodiment and also allows a difference in diameter between the treatment instrument channels to be recognized. This enables easy selection of operation instruments inserted through the respective operation instrument channels.

Two-channel scopes and other special apparatuses often have the suction port 19 arranged at positions different from those in typical apparatuses. The eleventh embodiment of the present invention is particularly effective in this case.

(Twelfth Embodiment)

Figure 31:
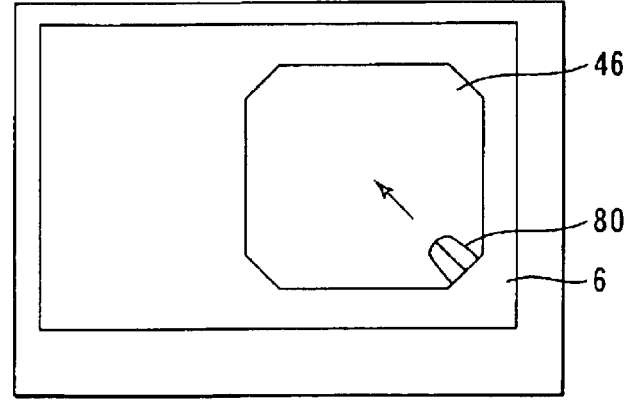
FIG. 31 is a plan view showing an observed image displayed on a monitor of an endoscope apparatus according to a twelfth embodiment of the present invention when a treatment instrument starts to be protruded.
Figure 32:
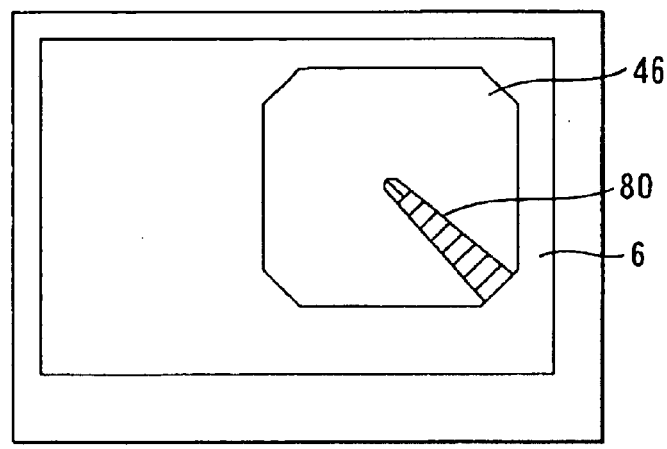
FIG. 32 is a plan view showing an observed image displayed on the monitor of the endoscope apparatus according to the twelfth embodiment of the present invention when the treatment instrument continues to be protruded.
Figure 33:
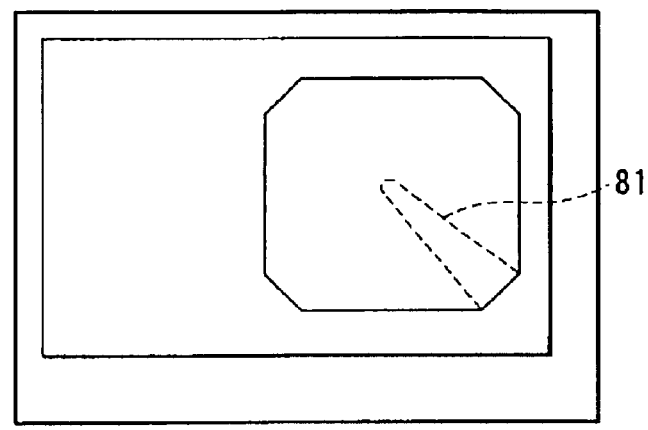
FIG. 33 is a plan view showing an observed image which is displayed on the monitor of the endoscope apparatus according to the twelfth embodiment of the present invention and which shows the range within which the treatment instrument is moved.

FIGS. 31 to 33 are plan views showing observed images displayed on a monitor of an endoscope apparatus according to a twelfth embodiment of the present invention. FIG. 31 shows an image observed when a treatment instrument starts to be protruded. FIG. 32 shows an image observed when the treatment instrument continues to be protruded. FIG. 33 shows an observed image showing the range within which the treatment instrument is moved. The entire configuration of the endoscope apparatus, which is not shown in FIGS. 31 to 33, will be described with reference to FIGS. 1 to 3.

In FIG. 1, in addition to information on the position of the suction port 19 in the end portion 17, the storage means 75 of the endoscope 2 of the twelfth embodiment stores operation instrument movement range information corresponding to the range within which the treatment instrument is moved when it is inserted through the treatment instrument channel and then protruded from of the suction port 19.

The display section 76 is configured to read the treatment instrument movement range information stored in the storage means 75 and to provide a treatment instrument movement range display 81, shown in FIG. 33, on an endoscope image on the screen of the monitor 6, the display 81 corresponding to the endoscope image and indicating at least part of the movement range of a treatment instrument 80, shown in FIGS. 31 and 32.

In this case, in this embodiment, the treatment instrument movement range display 81, shown in FIG. 33, indicates the outer periphery of a silhouette of the treatment instrument 80, shown in FIG. 32, using a broken line.

During examinations, as shown in FIG. 33, the observed image 46 shows the treatment instrument movement range display 81 specific to the endoscope. Thus, the operator can easily determine, in treating a lesion, where an image of the lesion should be placed on the endoscope image, without protruding the treatment instrument 80 from the suction port 19. This enables easy treatment.

The twelfth embodiment of the present invention provides an endoscope apparatus which not only produces the same effects as those of the tenth embodiment but also allows treatment to be easily carried out.

Figure 34:
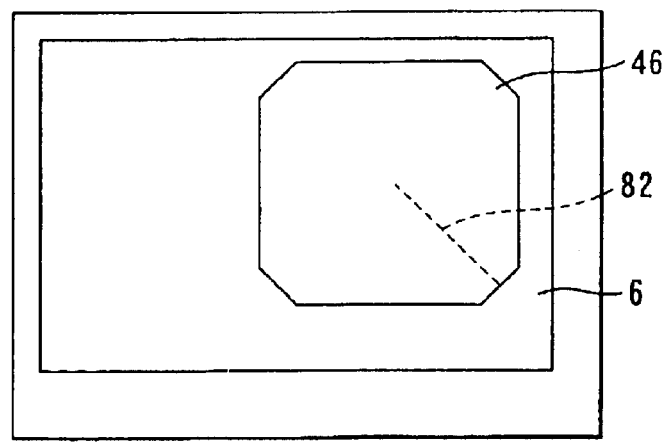
FIG. 34 is a plan view showing an observed image displayed on the monitor of the endoscope apparatus according to a variation of the twelfth embodiment of the present invention, shown in FIGS. 31 to 33.

FIG. 34 is a plan view showing an observed image displayed on the monitor of the endoscope apparatus according to a variation of the twelfth embodiment of the present invention, shown in FIGS. 31 to 33.

As shown in FIG. 34, in this variation, the observed image 46 on the monitor 6 shows a treatment instrument movement range display 82. The treatment instrument movement range display 82 shows a centerline of the treatment instrument 80, shown in FIG. 32, using a broken line.

During examinations, as shown in FIG. 34, the treatment instrument movement range 82 specific to the endoscope is displayed in the observed image 46.

Such a variation produces effects similar to those of the twelfth embodiment, shown in FIG. 33.

Like the eleventh embodiment, the twelfth embodiment and the treatment instrument movement range of its variation, shown in FIGS. 31 to 34, are particularly effective on endoscopes having two treatment instrument channels as well as other special apparatuses.

In the embodiments and variations shown in FIGS. 28 to 34, the storage means 75 stores the positional information on the suction port and the information on the movement range of the treatment instrument. However, the display section 76 of the video processor 5 may store in advance positional information on the suction port and information on the movement range of the treatment instrument both of which correspond to the name of the endoscope. In this case, the display section 76 reads information such as the name of the endoscope stored in the storage means 75 and identifying the endoscope. On the basis of this information, the display section 76 displays the suction port display 77, 78, 79a, or 79b of the suction port 19 or the treatment instrument movement range display 81 or 82.

Further, the treatment instrument movement range displays 81 and 82 are not necessarily based on the information on the movement range of the treatment instrument. If the direction in which the suction port 19 is open is substantially the same as the direction of the view, the treatment instrument movement range display may be displayed on the basis of only the positional information on the suction port 19, utilizing the nature that the protruded treatment instrument advances toward the center of the endoscope image.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A fitting jig of an endoscope hood member, the fitting jig comprising:
   a base section;
   a first position regulating section provided on the base section to regulate the position of the hood member with respect to the hood member fitting jig; and
   a second position regulating section provided on the base section to regulate the position of the hood member fitting jig with respect to an end section of the endoscope,
   wherein the first position regulating section has a first axial position regulating section that regulates the axial direction of the hood member with respect to the hood member fitting jig, and
   wherein the second position regulating section has a second axial position regulating section that regulates the axial direction of the hood member with respect to the end section of the endoscope.

2. The fitting jig of an endoscope hood member according to claim 1, wherein the hood member fitting jig further comprises a case member that accommodates the hood member.

3. The fitting jig of an endoscope hood member according to claim 2, wherein the case member is mounted on the base section.

4. The fitting jig of an endoscope hood member according to claim 1, wherein the hood member fitting jig further has a hood member fixing section that removably fixes the hood member to the hood member fitting jig.

5. A fitting jig of an endoscope hood member, the fitting jig comprising:
   a base section;
   a first position regulating section provided on the base section to regulate the position of the hood member with respect to the hood member fitting jig; and
   a second position regulating section provided on the base section to regulate the position of the hood member fitting jig with respect to an end section of the endoscope,
   wherein the first position regulating section has a first rotating direction regulating section that regulates the position of the hood member in a rotating direction with respect to the hood member fitting jig, and
   wherein the second position regulating section has a second rotating direction position regulating section that regulates the position of the hood member in the rotating direction with respect to the end section of the endoscope.

6. The fitting jig of an endoscope hood member according to claim 5, wherein the second rotating direction position regulating section is formed of a concave or convex section that engages with a convex or concave section formed on the end section of the endoscope.

7. The fitting jig of an endoscope hood member according to claim 5, wherein the second rotating direction position regulating section has an engaging section that engages with a suction port formed in the end section of the endoscope or a nozzle from which a fluid is ejected.

8. The fitting jig of an endoscope hood member according to claim 5, wherein the hood member fitting jig further has a hood member fixing section that removably fixes the hood member to the hood member fitting jig.

9. A fitting jig of an endoscope hood member, the fitting jig comprising:

a base section;

a first position regulating section provided on the base section to regulate the position of the hood member with respect to the hood member fitting jig; and a second position regulating section provided on the base section to regulate the position of the hood member fitting jig with respect to an end section of the endoscope, wherein the hood member fitting jig further comprises a case member that accommodates the hood member.

10. The fitting jig of an endoscope hood member according to claim 9, wherein the case member is mounted on the base section.

11. The fitting jig of an endoscope hood member according to claim 9, wherein the hood member fitting jig further has a hood member fixing section that removably fixes the hood member to the hood member fitting jig.

12. A fitting jig of an endoscope hood member, the fitting jig comprising:

a base section having a first position that abuts against an end section of the hood member when the hood member is mounted on the endoscope; and a projecting section which projects from the base section and has a second position that abuts against an end section of the endoscope when the hood member is mounted on the endoscope, wherein the hood member shaped generally like a cylinder is externally fitted over the projecting section so that an end section of the projecting section abuts against the end section of the endoscope, wherein the projecting section has an engaging section that engages with a suction port formed in the end section of the endoscope or a nozzle from which a fluid is ejected.

13. A fitting jig of an endoscope hood member, the fitting jig comprising:

a base section having a first position that abuts against an end section of the hood member when the hood member is mounted on the endoscope;

a projecting section which projects from the base section and has a second position that abuts against an end section of the endoscope when the hood member is mounted on the endoscope, wherein the hood member shaped generally like a cylinder is externally fitted over the projecting section so that an end section of the projecting section abuts against the end section of the endoscope, and a generally cylindrical outer diameter regulating section which has a diameter larger than that of the projecting section to project from the base section, and wherein the hood member is inserted between the outer diameter regulating section and the projecting section.

14. A fitting jig of an endoscope hood member to mount a hood member on an end section of an inserted section of an endoscope, the fitting jig comprising:

a base section;

first means provided on the base section for determining the position of the hood member relative to the hood member fitting jig; and second means provided on the base section for determining the position of the hood member fitting jig relative to the end section of the inserted section of the endoscope.

15. A fitting jig of an endoscope hood member, the fitting jig comprising:

a base section;

a first position determining section provided on the base section to determine the position of the hood member relative to the hood member fitting jig; and a second position determining section provided on the base section to determine the position of the hood member fitting jig relative to an end section of the endoscope.

16. The fitting jig of an endoscope hood member according to claim 15, wherein the first position determining section has a first axial position determining section that determines the axial direction of the hood member relative to the hood member fitting jig, and wherein the second position determining section has a second axial position determining section that determines the axial direction of the hood member relative to the end section of the endoscope.

17. The fitting jig of an endoscope hood member according to claim 16, wherein the hood member fitting jig further comprises a case member that accommodates the hood member.

18. The fitting jig of an endoscope hood member according to claim 17, wherein the case member is mounted on the base section.

19. The fitting jig of an endoscope hood member according to claim 15, wherein the first position determining section has a first rotating direction determining section that determines the position of the hood member in a rotating direction relative to the hood member fitting jig, and wherein the second position determining section has a second rotating direction position determining section that determines the position of the hood member in the rotating direction relative to the end section of the endoscope.

20. The fitting jig of an endoscope hood member according to claim 19, wherein the second rotating direction position determining section is formed of a concave or convex section that engages with a convex or concave section formed on the end section of the endoscope.

21. The fitting jig of an endoscope hood member according to claim 19, wherein the second rotating direction position determining section has an engaging section that engages with a suction port formed in the end section of the endoscope or a nozzle from which a fluid is ejected.

22. The fitting jig of an endoscope hood member according to claim 15, wherein the hood member fitting jig further comprises a case member that accommodates the hood member.

23. The fitting jig of an endoscope hood member according to claim 22, wherein the case member is mounted on the base section.

24. The fitting jig of an endoscope hood member according to claim 15, wherein the hood member fitting jig further has a hood member fixing section that removably fixes the hood member to the hood member fitting jig.

* * * * *